(12) United States Patent
Koseoglu et al.

(10) Patent No.: US 11,124,713 B2
(45) Date of Patent: Sep. 21, 2021

(54) PROCESS FOR FLUIDIZED CATALYTIC CRACKING OF DISULFIDE OIL TO PRODUCE ETHYLENE USED FOR METATHESIS TO PRODUCE PROPYLENE

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/386,741

(22) Filed: Apr. 17, 2019

(65) Prior Publication Data

US 2020/0332201 A1 Oct. 22, 2020

(51) Int. Cl.
*C10G 55/06* (2006.01)
*C07C 6/04* (2006.01)
*C10G 70/00* (2006.01)
*C10G 11/18* (2006.01)
*C07C 2/06* (2006.01)
(Continued)

(52) U.S. Cl.
CPC .............. *C10G 55/06* (2013.01); *C07C 2/06* (2013.01); *C07C 4/06* (2013.01); *C07C 4/08* (2013.01); *C07C 6/04* (2013.01); *C10G 11/18* (2013.01); *C10G 29/205* (2013.01); *C10G 70/00* (2013.01); *C07C 11/06* (2013.01); *C10G 2300/1077* (2013.01); *C10G 2300/202* (2013.01); *C10G 2400/20* (2013.01)

(58) Field of Classification Search
None
See application file for complete search history.

(56) References Cited

U.S. PATENT DOCUMENTS 3,074,878 A 1/1963 Pappas
4,419,221 A 12/1983 Castagnos et al.
(Continued)

FOREIGN PATENT DOCUMENTS

EP 0421701 A1 4/1991
WO 2009/015118 A2 1/2009
WO 2010/101686 A2 9/2010

OTHER PUBLICATIONS

Ziarifar et al. "New Design and Optimization for Replacing Dimethyl Disulfide with Wasted Disulfide Oil in Olefin Furnaces" Energy& Fuels 2018, 32, 11375-11382. (Year: 2018).*
(Continued)

*Primary Examiner* — Philip Y Louie
*Assistant Examiner* — Alyssa L Cepluch
(74) *Attorney, Agent, or Firm* — Abelman, Frayne & Schwab

(57) ABSTRACT

Relatively low value disulfide oil (DSO) compounds produced as by-products of the mercaptan oxidation (MEROX) processing of refinery hydrocarbon streams, and oxidized disulfide oils (ODSO), are economically converted to value-added light olefins by introducing the DSO and/or ODSO compounds as the feed to a fluidized catalytic cracking (FCC) unit and recovering the light olefins, namely, ethylene and propylene, and in some embodiments a minor amount of butylenes which is then recovered and introduced as the feedstream to a metathesis process for the production and recovery of propylene.

13 Claims, 4 Drawing Sheets

(51) Int. Cl.
    *C07C 4/06*     (2006.01)
    *C07C 4/08*     (2006.01)
    *C10G 29/20*     (2006.01)
    *C07C 11/06*     (2006.01)

(56) References Cited

U.S. PATENT DOCUMENTS

| | | | |
|---|---|---|---|
| 4,729,835 A * | 3/1988 | McNeillie | C02F 1/722 |
| | | | 210/759 |
| 4,980,053 A | 12/1990 | Li et al. | |
| 5,026,936 A | 6/1991 | Leyshon et al. | |
| 5,326,465 A | 7/1994 | Yongqing et al. | |
| 5,462,652 A | 10/1995 | Wegerer | |
| 5,981,818 A * | 11/1999 | Purvis | C07C 4/02 |
| | | | 526/75 |
| 6,656,346 B2 | 12/2003 | Ino et al. | |
| 7,220,886 B2 | 5/2007 | Podrebarac et al. | |
| 8,258,358 B2 | 9/2012 | Gartside et al. | |
| 2006/0089517 A1 | 4/2006 | Podrebarac | |
| 2006/0161033 A1 * | 7/2006 | Chodorge | C07C 11/06 |
| | | | 585/324 |
| 2007/0000808 A1 * | 1/2007 | Bhan | C10G 47/02 |
| | | | 208/58 |
| 2009/0030252 A1 * | 1/2009 | Senetar | C07C 4/06 |
| | | | 585/324 |
| 2010/0224534 A1 * | 9/2010 | Couch | C10G 11/18 |
| | | | 208/113 |
| 2018/0155642 A1 | 6/2018 | Al-Ghamdi et al. | |

OTHER PUBLICATIONS

International Search Report and Written Opinion dated Jun. 8, 2020 in counterpart International Application PCT/US2020/021637.

* cited by examiner

PROCESS FOR FLUIDIZED CATALYTIC CRACKING OF DISULFIDE OIL TO PRODUCE ETHYLENE USED FOR METATHESIS TO PRODUCE PROPYLENE

BACKGROUND OF THE INVENTION

Field of the Invention

This disclosure is directed to the processing of disulfide oil (DSO) compounds and their derivatives to produce light olefins, such as ethylene, that are subjected to a metathesis process to produce propylene.

Description of Related Art

FCC Process

Fluidized catalytic cracking (FCC) is a ubiquitous and very important process in hydrocarbon refinery operations. The FCC process catalytically converts, or cracks, hydrocarbon feedstocks boiling in the vacuum gas oil range, i.e., 370° C. to 520° C., without the addition of hydrogen to the conversion zone, which is typically operated at temperatures in the range of from about 480° C. to about 650° C. using a circulating stream of regenerated catalyst.

Fluidized catalytic cracking (FCC) process catalytically cracks the petroleum-derived hydrocarbons boiling in vacuum gas oil range with an acidic catalyst maintained in a fluidized state that is regenerated on a continuous basis. The principal product from the FCC process has generally been gasoline. Other products produced in smaller quantities via FCC processes include light hydrocarbons gases, C1-C4, and unconverted cycle oils. Coke deposited on the catalyst in the process is burned off in a fluidized regenerator at high temperatures, and in the presence of air prior to recycling the hot regenerated catalyst to the reaction zone.

The FCC process has the advantages of being performed without the addition of hydrogen and at relatively low operating pressure, i.e., 3 to 4 bars. However, the process requires relatively high reaction temperatures which accelerate conversion of some of the hydrocarbons to coke thereby decreasing the potentially greater volumetric yield of the normally liquid hydrocarbon product. This coke forms on the catalyst, and the FCC process requires the continuous regeneration of the catalyst by burning off the coke prior to the recycling of the catalyst. In recent years, in addition to the production of gasoline by FCC operations, there has been a growing interest in increasing the production of light olefins. The light olefins are valuable raw materials for various chemical processes and provide significant economic advantages to refiners, particularly with respect to oil refineries that are highly integrated with petrochemical production facilities.

There are different methods for producing light olefins by the FCC process. Some FCC operating conditions are based on a short contact time of the feedstock with the catalyst, e.g., as is disclosed in U.S. Pat. Nos. 4,419,221, 3,074,878, and 5,462,652. However, the short contact time between feedstock and catalyst typically results in a relatively low conversion of the feed.

Other FCC processes are based on using a catalyst additive such as pentasil-type zeolite, for instance, as is disclosed in U.S. Pat. No. 5,326,465. However, the use of a pentasil-type zeolite catalyst has the disadvantage of enhancing the yield of light fraction hydrocarbons at the expense of excessive cracking of the gasoline fraction, which is also a high value product.

Other FCC processes are based on carrying out the cracking reactions at high temperature, such as that disclosed in U.S. Pat. No. 4,980,053, which is incorporated herein by reference. However, this method can result in producing relatively high levels of dry gases.

Still other FCC processes are based on cracking the feed oil at a high temperature with a short contact time and using a catalyst mixture comprising a specific base cracking catalyst and an additive containing a shape-selective zeolite, such as disclosed in U.S. Pat. No. 6,656,346. Processes based on this method are known as High Severity Fluidized Catalytic Cracking (HS-FCC). Operating characteristics of this process include a down-flow reactor, high reaction temperatures, short contact time and high catalyst-to-oil ratio.

Downflow reactors permit higher catalyst-to-oil ratios because the lifting of the solid catalyst particles by vaporized feed as in upflow reactors is not required, and this is particularly suitable for HS-FCC. In addition, HS-FCC processes are operated under considerably higher reaction temperatures, e.g., 550° C. to 650° C. and shorter residence times, e.g., 0.1 to 1.0 seconds as compared to conventional FCC processes. Under these reaction temperatures, two competing cracking reactions occur, thermal cracking and catalytic cracking. Thermal cracking contributes to the formation of coke and of lighter products, such as dry gases, while the catalytic cracking increases propylene and butylenes yields. The short residence time in the downflow reactor also minimizes thermal cracking. Undesirable secondary reactions such as hydrogen transfer reactions which consume olefins are suppressed. The desired short residence time is attained by mixing and dispersing catalyst particles and feed at the reactor inlet followed by immediate separation at the reactor outlet. In order to compensate for the decrease in conversion due to the short contact time, the HS-FCC process is operated at relatively high catalyst-to-oil ratios.

Olefin Metathesis

Light olefins (C2-C4) are important chemical products that serve as building blocks for the petrochemical industry. For example, ethylene is used primarily to manufacture polyethylene and ethylene oxide, which are useful products in the packaging, plastic, construction and textile industries. Propylene is a building block in the production of polypropylene and many other chemical derivatives that are useful in plastic processing and the packaging and automotive sectors. Known processes for the production of light olefins include the steam pyrolysis of liquefied petroleum gas (LPG), naphtha, or other hydrogen rich streams and the fluidized catalytic cracking (FCC) of vacuum gas oils or atmospheric residues.

The demand for propylene is expected to grow at an even greater rate than the demand for ethylene. Technological developments such as the metathesis of ethylene and butylenes are becoming attractive to increase propylene production.

Commercial technologies currently available to produce propylene include steam cracking, fluid catalytic cracking (FCC), propane dehydrogenation, and metathesis of ethylene and butylenes, i.e., an olefin conversion technology.

The olefin metathesis process includes starting with separate two olefin substrates and forming them into a four-membered ring intermediate reaction product. The substituents on this four-membered ring are then rearranged to form two new carbon-carbon double bonds.

Olefin metathesis can convert ethylenes and butylenes into propylene. There are two principal equilibrium reactions occurring during the conversion process: first, the metathesis of ethylene and 2-butylene to produce propylene, followed by the isomerization of 1-butylene to 2-butylene as 2-butylene is consumed during the first equilibrium reaction listed above.

MEROX Process

The mercaptan oxidation process, commonly referred to as the MEROX process, has long been employed for the removal of the generally foul smelling mercaptans found in many hydrocarbon streams and was introduced in the refining industry over fifty years ago. Because of regulatory requirements for the reduction of the sulfur content of fuels for environmental reasons, refineries have been, and continue to be faced with the disposal of large volumes of sulfur-containing by-products.

Disulfide oil (DSO) compounds are produced as a by-product of the MEROX process in which the mercaptans are removed from any of a variety of petroleum streams including liquefied petroleum gas, naphtha, and other hydrocarbon fractions. It is commonly referred to as a 'sweetening process' because it removes the sour or foul smelling mercaptans present in crude petroleum. The term "DSO" is used for convenience in this description and in the claims, and will be understood to include the mixture of disulfide oils produced as by-products of the mercaptan oxidation process.

As noted above, the designation "MEROX" originates from the function of the process itself, i.e., the conversion of mercaptans by oxidation. The MEROX process in all of its applications is based on the ability of an organometallic catalyst in a basic environment, such as a caustic, to accelerate the oxidation of mercaptans to disulfides at near ambient temperatures and pressures. The overall reaction can be expressed as follows:

$$RSH + \tfrac{1}{4}O_2 \rightarrow \tfrac{1}{2}RSSR + \tfrac{1}{2}H_2O \tag{1}$$

where R is a hydrocarbon chain that may be straight, branched, or cyclic, and the chains can be saturated or unsaturated. In most petroleum fractions, there will be a mixture of mercaptans so that the R can have 1, 2, 3 and up to 10 or more carbon atoms in the chain. This variable chain length is indicated by R and R' in the reaction. The reaction is then written:

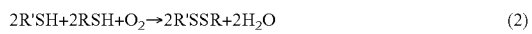

$$2R'SH + 2RSH + O_2 \rightarrow 2R'SSR + 2H_2O \tag{2}$$

This reaction occurs spontaneously whenever any sour mercaptan-bearing distillate is exposed to atmospheric oxygen, but proceeds at a very slow rate. In addition, the catalyzed reaction (1) set forth above requires the presence of an alkali caustic solution, such as aqueous sodium hydroxide. The mercaptan oxidation proceeds at an economically practical rate at moderate refinery downstream temperatures.

The MEROX process can be conducted on both liquid streams and on combined gaseous and liquid streams. In the case of liquid streams, the mercaptans are converted directly to disulfides which remain in the product so that there is no reduction in total sulfur content of the effluent stream.

The MEROX process typically utilizes a fixed bed reactor system for liquid streams and is normally employed with charge stocks having end points above 135° C.-150° C. Mercaptans are converted to disulfides in the fixed bed reactor system over a catalyst, for example, an activated charcoal impregnated with the MEROX reagent, and wetted with caustic solution. Air is injected into the hydrocarbon feedstream ahead of the reactor and in passing through the catalyst-impregnated bed, the mercaptans in the feed are oxidized to disulfides. The disulfides are substantially insoluble in the caustic and remain in the hydrocarbon phase. Post treatment is required to remove undesirable by-products resulting from known side reactions such as the neutralization of $H_2S$, the oxidation of phenolic compounds, entrained caustic, and others.

The vapor pressures of disulfides are relatively low compared to those of mercaptans, so that their presence is much less objectionable from the standpoint of odor; however, they are not environmentally acceptable due to their sulfur content and their disposal can be problematical.

In the case of mixed gas and liquid streams, extraction is applied to both phases of the hydrocarbon streams. The degree of completeness of the mercaptan extraction depends upon the solubility of the mercaptans in the alkaline solution, which is a function of the molecular weight of the individual mercaptans, the extent of the branching of the mercaptan molecules, the concentration of the caustic soda and the temperature of the system. Thereafter, the resulting DSO compounds are separated and the caustic solution is regenerated by oxidation with air in the presence of the catalyst and reused.

Referring to the attached drawings, FIG. 1 is a simplified schematic of a generalized conventional version of a MEROX process of the prior art employing liquid-liquid extraction for removing sulfur compounds in an embodiment in which a combined propane and butane hydrocarbon stream (1) containing mercaptans is treated and which includes the steps of:

introducing the hydrocarbon stream (1) with a homogeneous cobalt-based catalyst into an extraction vessel (10) containing a caustic solution (2);

passing the hydrocarbon catalyst stream in counter-current flow through the extraction section of the extraction (10) vessel in which the extraction section includes one or more liquid-liquid contacting extraction decks or trays (not shown) for the catalyzed reaction with the circulating caustic solution to convert the mercaptans to water soluble alkali metal alkane thiolate compounds;

withdrawing a hydrocarbon product stream (3) that is free or substantially free of mercaptans from the extraction vessel (10);

recovering a combined spent caustic and alkali metal alkane thiolate stream (4) from the extraction vessel (10);

subjecting the spent caustic to catalyzed wet air oxidation in a reactor (20) into which is introduced catalyst (5) and air (6) to provide the regenerated spent caustic (8) and convert the alkali metal alkane thiolate compounds to disulfide oils; and recovering a by-product stream (7) of disulfide oil (DSO) compounds and a minor proportion of other sulfides such as mono-sulfides and tri-sulfides.

The effluents of the wet air oxidation step in the MEROX process preferably comprise a minor proportion of sulfides and a major proportion of disulfide oils. As is known to those skilled in the art, the composition of this effluent stream depends on the effectiveness of the MEROX process, and sulfides are assumed to be carried-over material. A variety of catalysts have been developed for the commercial practice of the process. The efficiency of the MEROX process is also a function of the amount of $H_2S$ present in the stream. It is a common refinery practice to install a prewashing step for $H_2S$ removal.

The disulfide oil compounds produced in the MEROX process can contain various disulfides. For example, a MEROX unit designed for the recovery of propane and butane yields a disulfide oil mixture with the composition set forth in Table 1:

TABLE 1

| Disulfide Oil | W % | BP, °C. | MW, g/g-mol | Sulfur, W % |
|---|---|---|---|---|
| Dimethyldisulfide | 15.7 | 110 | 94 | 68.1 |
| Diethyldisulfide | 33.4 | 152 | 122 | 52.5 |
| Methylethyldisulfide | 49.3 | 121 | 108 | 59.3 |
| Total (Average) | 98.4 | (127) | (109) | (57.5) |

Table 1 indicates the composition of the disulfide oil that is derived from semi-quantitative GC-MS data. No standards were measured against the components; however, the data in Table 1 is accurate as representing relative quantities. Quantitative total sulfur content was determined by energy dispersive x-ray fluorescence spectroscopy which indicated 63 W % of sulfur, and this value will be used in later calculations. The GC-MS results provide evidence of trace quantities of tri-sulfide species; however, the majority of the disulfide oil stream comprises the three components identified in Table 1.

The by-product disulfide oils produced by the MEROX unit can be processed and/or disposed of in various other refinery units' operations. For example, the DSO can be added to the fuel oil pool at the expense of a resulting higher sulfur content of the pool. The DSO can be processed in a hydrotreating/hydrocracking unit at the expense of higher hydrogen consumption. The disulfide oil also has an unpleasant foul or sour smell, which is somewhat less prevalent because of its relatively lower vapor pressure at ambient temperature; however, problems exist in the handling of this oil.

By-product disulfide oil (DSO) compounds from the mercaptan oxidation process can be oxidized, preferably in the presence of a catalyst, and constitute an abundant source of the oxidized disulfide oil (ODSO) compounds that are sulfoxides, sulfonates, sulfonates and sulfones. The oxidant can be a liquid peroxide selected from the group consisting of alkyl hydroperoxides, aryl hydroperoxides, dialkyl peroxides, diaryl peroxides, peresters and hydrogen peroxide. The oxidant can also be a gas, including air, oxygen, ozone and oxides of nitrogen. The catalyst is preferably a homogeneous water-soluble compound that is a transition metal containing an active species selected from the group consisting of Mo (VI), W (VI), V (V), Ti (IV), and their combination.

The ODSO compounds have been found to have utility as lubricity additives for diesel fuels that are more economical than currently available additives for that purpose, and also as solvents for aromatic solvent extraction processes. In the event that a refiner has produced or has on hand an amount of DSO compounds that is in excess of foreseeable needs for these or other uses, the refiner may wish to dispose of the DSO compounds in order to clear a storage vessel and/or eliminate the product from inventory for tax reasons.

Thus, there is a clear and long-standing need to provide an efficient and economical process for the treatment of the large volumes of DSO by-products and their derivatives to effect and modify their properties in order to facilitate and simplify their environmentally acceptable disposal, and/or to permit the utilization of the modified products within the refinery, and thereby enhance the value of this class of by-products to the refiner.

SUMMARY OF THE INVENTION

The above needs are met and other advantages are provided by the process of the present invention that economically converts disulfide oils and their derivatives, oxidized disulfide oils, which are of relatively low value, to value-added light olefins by introducing the DSO compounds as the feed to a fluidized catalytic cracking unit and recovering the light olefins, namely, ethylene and propylene, and in some embodiments a minor amount of butylenes which are then recovered and introduced as the feedstream to a metathesis process for the production and recovery of propylene.

In an embodiment, the present disclosure is directed to an integrated refinery process for removing mercaptans from a hydrocarbon stream containing mercaptans, the process comprising:

introducing the hydrocarbon stream containing mercaptans into an extraction vessel containing an alkaline solution;

passing the hydrocarbon stream through an extraction section of the extraction vessel which includes one or more liquid-liquid contacting decks for reaction which converts the mercaptans to water soluble compounds;

withdrawing a hydrocarbon product stream free of mercaptans from the extraction vessel;

recovering a spent caustic solution containing sulfur compounds from the extraction vessel;

subjecting the spent caustic sulfur-containing solution to air oxidation to produce waste water and a by-product stream containing disulfide oils and sulfides;

separating the disulfide oils and sulfides from the waste water;

introducing the disulfide oil (DSO) stream into a fluidized catalytic cracking (FCC) unit to produce the light olefins ethylene, propylene and butylenes; and passing the light olefins to a metathesis processing unit to increase propylene production.

The process and apparatus of the present disclosure enables refiners and gas plant operators to convert waste disulfide oils to one or more value-added products. It will be understood that the amount of the disulfide oils introduced into the FCC unit is not critical and that the amount may vary based upon its availability, e.g., as produced by other refinery processes and/or the capacity of storage tanks, and the disulfide oil-containing stream can comprise disulfide oils in the range of 1 V % to 100 V %.

In the description that follows, the terms "disulfide oil", "DSO", "DSO mixture" and "DSO compounds" may be used interchangeably for convenience.

In the description that follows, the terms "oxidized disulfide oil", "derivative of disulfide oil", "ODSO", "ODSO mixture" and "ODSO compound(s)" may be used interchangeably for convenience.

In the description that follows, the terms "DSO/ODSO", "DSO/ODSO mixture" and "DSO/ODSO compound(s)" may be used interchangeably for convenience.

BRIEF DESCRIPTION OF THE DRAWINGS

The process of the disclosure will be described in more detail below and with reference to the attached drawings in which the same number is used for the same or similar elements, and where.

DETAILED DESCRIPTION OF PREFERRED EMBODIMENTS

The process of the present disclosure for treating by-product disulfide oils in an integrated FCC/metathesis process will be described with reference to FIGS. 2-4.

Figure 1:
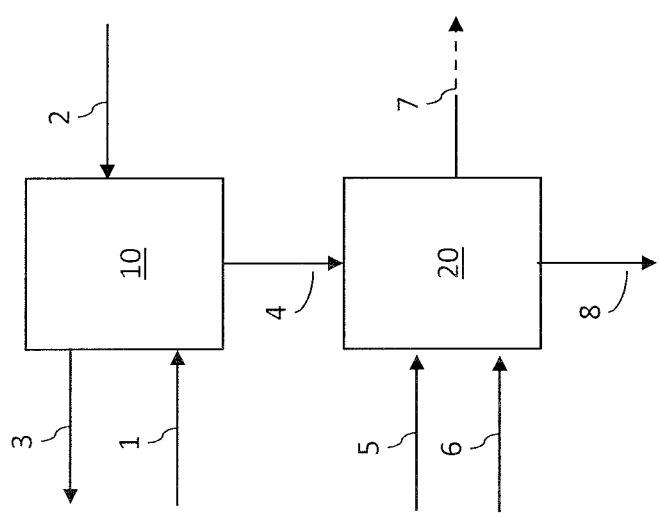
FIG. 1 is a simplified schematic diagram of a generalized version of the mercaptan oxidation or MEROX process of the prior art for the liquid-liquid extraction of a combined propane and butane stream.
Figure 2:
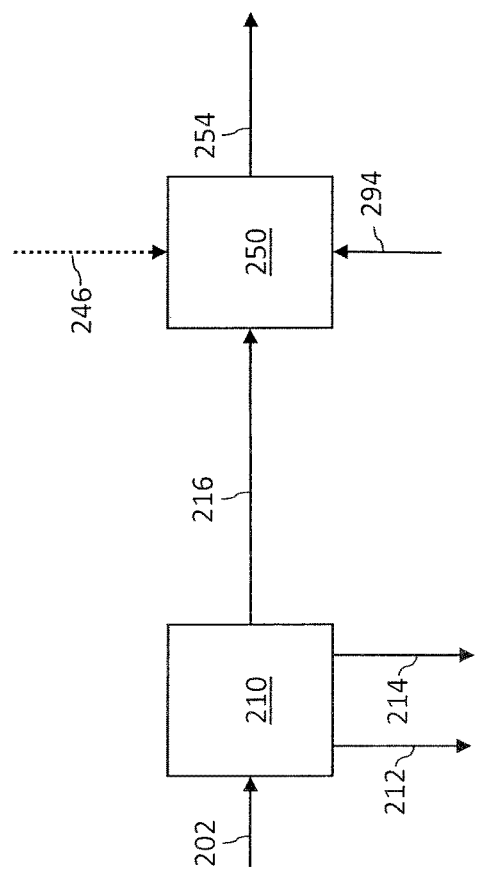
FIG. 2 is a simplified schematic diagram of a first embodiment of the integrated FCC/metathesis process of the present disclosure.

With reference to FIG. 2, the process and system, which for convenience is referred to as "Embodiment 1", includes an FCC unit (210) and a metathesis unit (250). A DSO stream or a separate ODSO stream, or an appropriately mixed DSO/ODSO stream (202) is introduced into the FCC unit (210) for cracking. Due to their immiscibility, in some embodiments where a mixed DSO/ODSO stream is used, the DSO and ODSO components can be introduced into the FCC unit (210) via separate inlets (not shown). The catalyst (212) is passed from the reaction zone to the regenerator to burn off the coke formed and the cracked liquid hydrocarbon stream (214) is recovered for downstream separation by conventional means known in the art. As is known in the art, the catalyst is typically recycled after regeneration and mixed with fresh catalyst in an amount needed to compensate process losses.

In some embodiments, not shown, some or all of the cracked liquid hydrocarbon stream (214) can be recycled and mixed with stream (202) since there may be some unconverted DSO components carried over with the product. Some or all of the cracked liquid hydrocarbon stream (214) can be sent to downstream refinery processes such as a hydrodesulfurization unit (not shown).

An ethylene-rich lower olefin gas stream (216) recovered from the FCC unit (210) is introduced into the metathesis reactor unit (250). The ethylene-rich gas stream (216) comprises ethylene, propylene, butylenes and methane. In an embodiment, additional butylenes (294) and, optionally, additional ethylene (246) can be introduced into the metathesis unit (250) for reaction with the ethylene-rich gas product (216). Sources of these additional optional streams can include refinery operations such as stream pyrolysis or steam cracking of ethane, LPG, naphtha, and the like. A propylene-rich product stream (254) is recovered from the metathesis unit (250).

Figure 3:
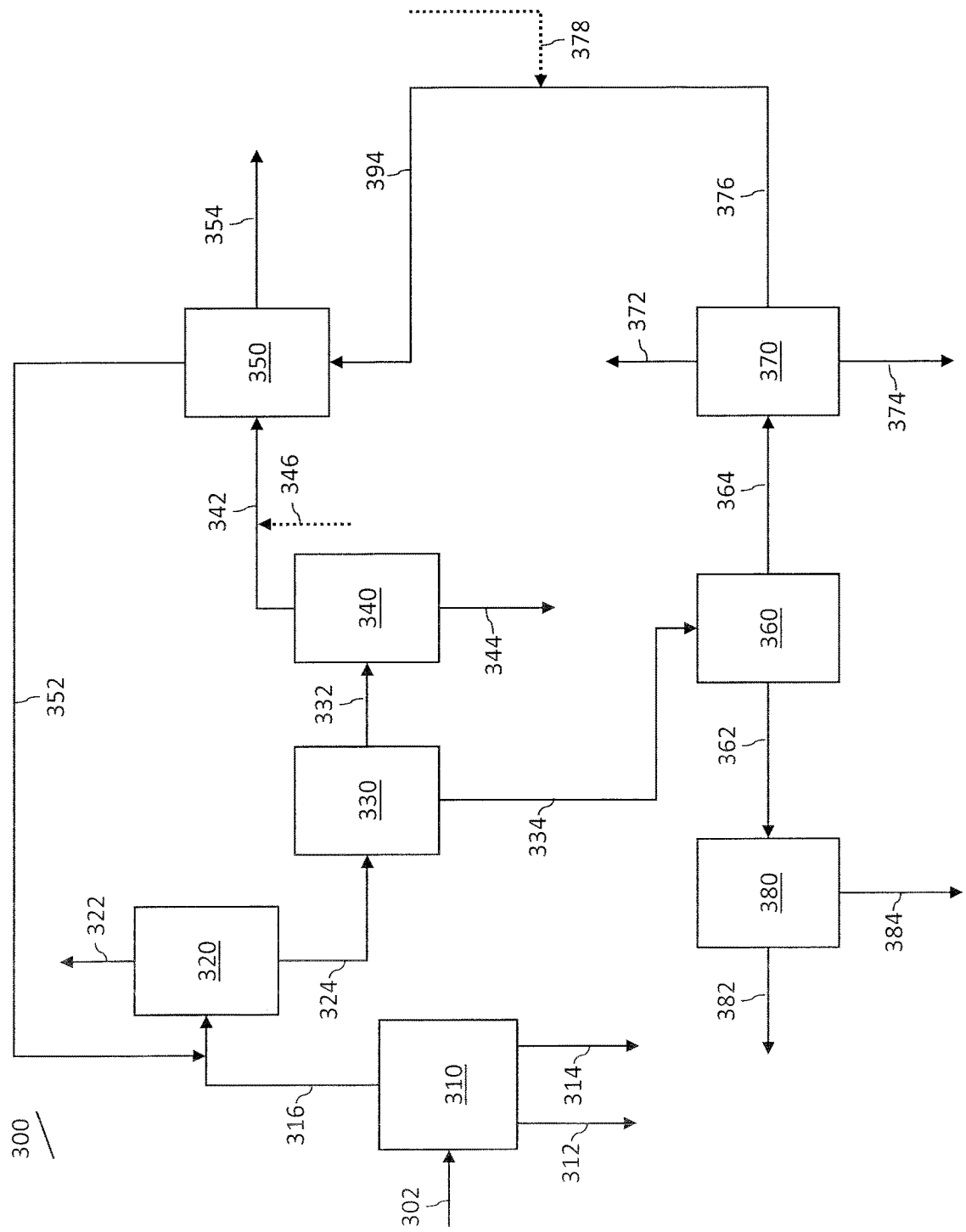
FIG. 3 is a simplified schematic diagram of a second embodiment of the integrated FCC/metathesis process of the present disclosure.

Referring now to FIG. 3, for convenience the process and system of a second embodiment, referred to as "Embodiment 2", includes an FCC unit (310), a demethanizing unit (320), a deethanizing unit (330), a depropanizing unit (360), a C2 splitter (340), a C3 splitter (380), a metathesis unit (350), and a fractionation unit (370).

A DSO stream, an ODSO stream or a mixed DSO/ODSO stream (302) is introduced into the FCC unit (310) for cracking. Due to their immiscibility, in some embodiments where a mixed DSO/ODSO stream is used, the DSO and ODSO components can be introduced into FCC unit (310) via separate inlets (not shown). The catalyst (312) is passed from the reaction zone to the regenerator to burn off the coke formed and the cracked liquid hydrocarbon stream (314) is recovered for separation downstream by conventional means known in the art. After regeneration, the hot catalyst can be mixed upstream of the reactor/reaction zone with fresh catalyst in an amount needed to compensate for catalyst process losses in order to maintain production goals and product quality.

In some embodiments, not shown, some or all of the cracked liquid hydrocarbon stream (314) can be recycled and mixed with stream (302) since some unconverted DSO components may have carried over with the product. Some or all of the cracked liquid hydrocarbon stream (314) can be sent to downstream refinery processes such as a hydrodesulfurization unit.

The gaseous products stream (316) from the FCC unit (310) is introduced into a demethanizer unit (320). A hydrogen and methane stream (322) is removed and the remaining stream comprising hydrocarbons with two or more carbons (324), i.e., a C2+ stream, is introduced into a deethanizer unit (330). The deethanizer unit (330) separates an ethane and ethylene stream (332) from a stream comprising hydrocarbons with three or more carbons (334), i.e., a C3+ stream.

The ethane and ethylene stream (332) is fed to a C2 splitter unit (340) for recovery of an ethylene stream (342) and a separate ethane stream (344) that is removed from the system.

The C3+ stream (334) is introduced into a depropanizer unit (360) where a combined propane and propylene stream (362) is separated from a stream comprising hydrocarbons with four or more carbons (364), i.e., a C4+ stream. The propane and proplyene stream (362) is sent to a C3 splitter unit (380) for separation and recovery of separate propylene (382) and propane (384) streams, which are removed from the system.

The C4+ stream (364) is introduced into a fractionation unit (370) where an isobutylenes stream (372), a butylenes stream (376), and a stream comprising hydrocarbons with five or more carbons (374), i.e., a C5+ stream, are separated. The butylenes stream (376) can optionally be combined with an additional butylenes stream (378) to form a combined butylenes stream (394). In embodiments where an additional butylenes stream is not introduced, combined butylenes stream (394) will comprise only the separated butylenes stream (376).

The ethylene stream (342) from the C2 splitter (340), and optionally, an additional ethylene stream (346), and the combined butylenes stream (394) are introduced into a metathesis unit (350) for conversion to a propylene-rich product stream (354). Sources for the additional ethylene can include refinery operations such as steam cracking or pyrolysis units.

A propylene-rich product stream (354) is recovered from the metathesis unit (350) and a metathesis effluents stream (352) is recycled for combination with the gas products stream (316) from the FCC unit (310) before introduction to the demethanizer unit (320). Some or all of the metathesis effluents stream (352) can be bled from the system. In some embodiments, 5-10 W % of the metathesis effluents stream (352) is bled from the system. In some embodiments, metathesis effluents stream (352) comprises a major proportion of propylene, e.g., approximately 80 wt %, and about 6 to 8 W % each of ethane, methane and the butanes.

In some embodiments (not shown), the metathesis effluents stream (352) is not recycled and instead is introduced into a separate fractionation section that includes a deethanizer, depropanizer and debutanizer in order to recover a C2− stream, a C3− stream, a C4− stream, and a C4+ stream, respectively.

Figure 4:
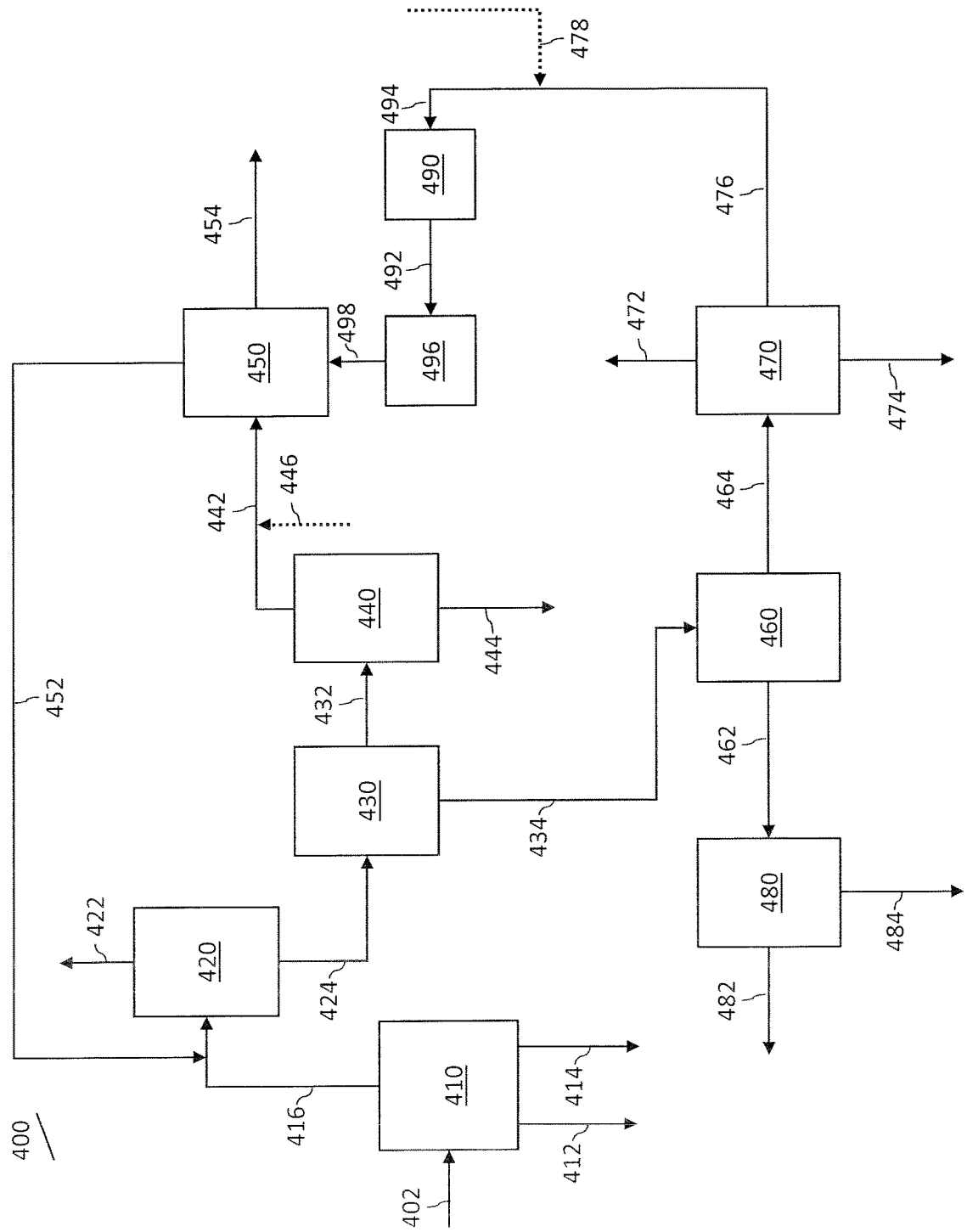
FIG. 4 is a simplified schematic diagram of a third embodiment of the integrated FCC/metathesis process of the present disclosure.

Referring now to FIG. 4, the process and system of a third embodiment, for convenience referred to as "Embodiment 3", includes an FCC unit (410), a demethanizer unit (420), a deethanizer unit (430), a depropanizer unit (460), a C2 splitter (440), a C3 splitter (480), a metathesis unit (450), a fractionation unit (470), a selective hydrogenation unit (490), and hydroisomerization unit (496).

A DSO stream, an ODSO stream or a mixed DSO/ODSO stream (402) is introduced into the FCC unit (410) for cracking. Due to their immiscibility, in some embodiments where a mixed DSO/ODSO stream is used, the DSO and ODSO components can be introduced into FCC unit (310) via separate inlets (not shown). The catalyst (412) is passed from the reaction zone to the regenerator to burn off the coke formed and the cracked liquid hydrocarbon stream (414) is recovered for downstream separation by conventional means known in the art. As was noted above, the catalyst is returned to the reactor after regeneration and mixed, as needed, with fresh catalyst in an amount required to compensate for catalyst process losses in order to maintain production goals and product quality.

In some embodiments, not shown, some or all of the cracked liquid hydrocarbon stream (414) can be recycled and mixed with stream (402) since some unconverted DSO components may have carried over with the product. Some or all of the cracked liquid hydrocarbon stream (414) can be sent to downstream refinery processes such as a hydrodesulfurization unit.

The gas products stream (416) from the FCC unit (410) is introduced into a demethanizing unit (420) where a hydrogen and methane stream (422) is removed and the remaining stream comprising hydrocarbons with two or more carbons (424), i.e., a C2+ stream, is introduced into a deethanizing unit (430) to separate a combined ethane and ethylene stream (432) from a stream (434) comprising hydrocarbons with three or more carbons, i.e., a C3+ stream.

The ethane and ethylene stream (432) is fed to a C2 splitter unit (440) where an ethane stream (444) is separated from an ethylene stream (442), the ethane (444) can be removed from the system for other uses.

The C3+ stream (434) is introduced into a depropanizing unit (460) where a propane and propylene stream (462) is separated from a stream comprising hydrocarbons with four or more carbons (464), i.e., a C4+ stream. The propane and propylene stream (462) is sent to a C3 splitter unit (480) for separation of propylene (482) and propane (484). The propylene stream (482) and the propane (484) are removed from the system.

The C4+ stream (464) is introduced into a fractionation unit (470) where an iso-butylene stream (472), a butylenes stream (476), and a stream comprising hydrocarbons with five or more carbons (474), i.e., a C5+ stream, are separated. The butylenes stream (476) can optionally be combined with an additional butylenes stream (478) to form a combined butylenes stream (494). In embodiments where additional butylenes are not introduced, combined butylenes stream (494) will simply comprise the separated butylenes stream (476).

The combined butylenes stream (494) and hydrogen (not shown) are introduced into a selective hydrogenation unit (490) for the conversation of any 1,3-butadiene in the combined butylenes stream (494) to butylenes which is recovered as butylenes effluent stream (492). After processing in the selective hydrogenation unit (490) all or substantially all of the 1,3-butadiene in the combined butylenes stream (494) is converted. In certain embodiments, hydrogen from the hydrogen and methane stream (422) can be used as a supplemental source of hydrogen.

The butylenes effluent stream (492) is introduced into a hydroisomerization unit (496) in order to convert 1-butylene into 2-butylene and produce an enhanced butylenes effluent stream (498).

The ethylene stream (442) from the C2 splitter (440) and, optionally, an additional ethylene stream (446), and the enhanced butylenes effluent stream (498) are introduced into a metathesis unit (450) for conversion into a propylene-rich product stream (454) which is recovered, and a metathesis unit effluent stream (452) is optionally recycled for combination with the gas products stream (416) from the FCC unit (410) before introduction to the demethanizer unit (420). Alternatively, some or all of the metathesis effluents stream (452) can be bled from the system. In some embodiments, 5-10 W % of the metathesis effluents stream (452) is bled from the system.

In some embodiments (not shown), the metathesis unit effluent stream (452) is not recycled and instead is introduced into a separate fractionation section including a deethanizer, depropanizer, debutanizer in order to recover a C2− stream, a C3− stream, a C4− stream, respectively, for use in the process as described above, and a C4+ stream.

As will be apparent to a person of ordinary skill in the art, Embodiments 1, 2 and 3 are directed to a system and process where either all of the gaseous products from an FCC reactor are sent directly to a metathesis unit in order to increase propylene production, i.e., Embodiment 1, or where the gas products from an FCC reactor are first fractionated before being sent to a metathesis unit in order to increase propylene production, i.e., Embodiments 2 and 3. This disclosure is also directed to embodiments (not shown) that encompass other obvious permutations of Embodiment 1 and Embodiments 2 and 3.

The FCC unit can operate at a temperature in the range of from about 450° C. to 700° C., 500° C. to 650° C., or 530° C. to 620° C.; at a pressure in the range of from about 1 bar to 20 bars, 1 bar to 10 bars, or 1 bar to 3 bars; at a residence time in the range of from about 0.1 sec to 30 sec, 0.1 sec to 10 sec, or 0.2 sec to 0.7 sec; and at a catalyst-to-oil weight ratio in the range of from about 1:1 to 40:1, 1:1 to 20:1, or 1:1 to 6:1

The metathesis unit can operate at a pressure in the range of from about 10 mbar to 100 bars, 10 mbar to 60 bars, or 10 mbar to 30 bars; at a residence time in the range of from 0.1 min to 60 min, 30 min to 60 min, or 15 min to 30 min; and at a GHSV in the range of from 1 $hr^{-1}$ to 5000 $hr^{-1}$, 10 $hr^{-1}$ to 3000 $hr^{-1}$, or 100 $hr^{-1}$ to 2000 $hr^{-1}$. In embodiments where a tungsten-based catalyst is used, the metathesis unit can operate at a temperature in the range of from about 300° C. to 500° C., 350° C. to 450° C., or 375° C. to 450° C. In embodiments where a rhenium- or ruthenium-based catalyst is used, the metathesis unit can operate at a temperature in the range of from about 20° C. to 200° C., 20° C. to 150° C., or 20° C. to 100° C. In some embodiments, catalysts used in the metathesis unit include tungsten oxide on a silica support. In some embodiments, rhenium oxide and ruthenium oxide catalysts can be used.

The demethanizer unit, the deethanizer unit, the depropanizer unit and the C3 splitter are typically separation columns operating on the differences in boiling points of components in the streams to be separated from each other, i.e., methane (−161.5° C.), ethane (−89° C.), propane (−42° C.), propylene (47.6° C.), and also from other higher boiling point gases.

In some embodiments, the fractionation unit is a distillation column that separates C4 from other higher boiling hydrocarbons. The column is typically designed with at least 15 theoretical plates to achieve efficient separation.

The selective hydrogenation unit can operate at a temperature in the range of from about 20° C. to 200° C., 20° C. to 150° C., or 20° C. to 120° C.; at a pressure in the range of from about 1 bar to 40 bars, 5 bars to 35 bars, or 10 bars to 30 bars; at a GHSV in the range of from about 100 hr$^{-1}$ to 20,000 hr$^{-1}$, 300 hr$^{-1}$ to 15,000 hr$^{-1}$, or 500 hr$^{-1}$ to 10,000 hr$^{-1}$; at a LHSV in the range of from about 0.1 hr$^{-1}$ to 100 hr$^{-1}$, 0.5 hr$^{-1}$ to 50 hr$^{-1}$, or 1.0 hr$^{-1}$ to 25 hr$^{-1}$; and at a hydrogen-to-diene molar ratio in the range of from about 1:1 to 10:1, 1:1 to 5:1, or 1:1 to 2:1. In some embodiments, catalysts used in the selective hydrogenation unit include those that are nickel-based, active phase, on an alumina support.

The hydroisomerization unit operates at a temperature in the range of from about 100° C. to 400° C., 100° C. to 300° C., or 100° C. to 200° C.; at a pressure in the range of from about 1 bar to 80 bars, 1 bar to 50 bars, or 1 bar to 30 bars; at a LHSV in the range of from about 0.5 hr$^{-1}$ to 8.0 hr$^{-1}$, 0.5 hr$^{-1}$ to 5.0 hr$^{-1}$, or 0.5 hr$^{-1}$ to 2.0 hr$^{-1}$; and at a hydrogen-to-oil volumetric ratio in the range of from about 100 to 1000 L/L, 100 to 500 L/L, or 100 to 200 L/L.

The DSO feed, ODSO feed or mixed DSO/ODSO feedstream can be processed together with other conventional FCC feedstocks including, but not limited to vacuum gas oils boiling in the range of from 350° C. to 565° C., deasphalted oils from a solvent deasphalting unit boiling above 520° C., delayed coker gas oils boiling in the range similar to vacuum gas oils, i.e., up to about 565° C., hydrocracker bottoms, or atmospheric residues boiling above 350° C.

The DSO feed, ODSO feed or mixed DSO/ODSO feedstream can comprise an amount in the range of from 1 V % to 100 V % of the initial feedstock. The FCC unit can have a pretreatment unit, i.e., a VGO hydrotreater operating with a hydrogen partial pressure in the range of from 30 bar to 70 bar upstream of the FCC unit to improve the quality of the feedstock.

Example 1

A disulfide oil sample, the properties and composition of which are provided in Table 1, was subjected to a fluidized catalytic cracking process using a Micro Activity Test (MAT) unit. The MAT runs were conducted in a fixed-bed reactor according to ASTM D51549 entitled "Determining Activity and Selectivity of FCC Catalysts by Microactivity Test". A proprietary FCC catalyst based on USY zeolite was used for the tests. The catalyst comprises a zeolite as an active component and clay as filler, both having microporosity and alumina, and silica as binders having mesoporosity, The catalyst was conditioned according to ASTM D4463 entitled "Metals-Free Steam Deactivation of Fresh Fluid Cracking Catalyst". According to this method, the catalyst used was aged at 810° C. and ambient pressure, i.e., at 1 bar, under a flow of 100% steam for 6 hours. Two tests were conducted at catalyst-to-oil (C/O) ratios of 3.36 and 3.26 and under conventional FCC conditions, i.e., 530° C. Table 2 indicates the product yields.

TABLE 2

|  | Run 1 | Run 2 | Average |
|---|---|---|---|
| Temperature ° C. | 530 | 530 | 530 |
| Catalyst/Oil Ratio | 3.36 | 3.26 | 3.31 |
| Gas Yields, W % |  |  |  |
| H2 | 0.0 | 0.0 | 0.0 |
| Methane | 3.6 | 3.7 | 3.6 |
| Ethane | 4.3 | 4.2 | 4.3 |
| Ethylene | 16.9 | 17.1 | 17.0 |
| Propane | 0.1 | 0.1 | 0.1 |
| Propylene | 3.5 | 2.9 | 3.2 |
| Butanes | 0.1 | 0.1 | 0.1 |
| Butylenes | 0.7 | 0.7 | 0.7 |
| 1,3-Butadiene | 0.1 | 0.1 | 0.1 |
| Total Gas | 29.3 | 28.8 | 29.0 |
| Total Gas | 29.3 | 28.8 | 29.0 |
| Total Liquid Products | 63.6 | 64.0 | 63.8 |
| Coke | 7.1 | 7.2 | 7.2 |
| Total | 100.0 | 100.0 | 100.0 |

As indicated by the data in Table 2, at 530° C. and a catalyst-to-oil ratio of 3.31, on average the fluidized catalytic cracking of the DSO samples yielded 17.0 W % of ethylene, 3.2 W % of propylene and 0.7 W % butylenes for a total yield of about 21 W % of light olefins.

Example 2

The light olefins produced according to the procedure of Example 1 were then subjected to metathesis according to Embodiment 1 as described above at a temperature of 400° C. and a pressure of 60 bars over a tungsten on silica catalyst.

Table 3 summarizes the material balance for the integrated FCC and metathesis process. No supplemental ethylene was added in Example 2.

TABLE 3

| Stream Name | DSO | Total liquid products | Coke | Ethylene rich gas Stream | C4 Feed | Propylene rich gas stream |
|---|---|---|---|---|---|---|
| Corresponding Reference Number | 202 | 214 | 212 | 216 | 294 | 254 |
| Temperature ° C. |  |  |  | 530 |  |  |
| Catalyst/Oil Ratio |  |  |  | 3.31 |  |  |
| Gas Yields, W % |  |  |  |  |  |  |
| DSO | 100.00 |  |  |  |  |  |
| H2 |  |  |  | 0.00 |  | 0.00 |
| Methane |  |  |  | 3.64 |  | 3.64 |
| Ethane |  |  |  | 4.25 |  | 4.25 |
| Ethylene |  |  |  | 16.98 |  | 0.05 |
| Propane |  |  |  | 0.08 |  | 0.08 |
| Propylene |  |  |  | 3.20 | 0.00 | 43.68 |

TABLE 3-continued

| Stream Name | DSO | Total liquid products | Coke | Ethylene rich gas Stream | C4 Feed | Propylene rich gas stream |
|---|---|---|---|---|---|---|
| Butanes | | | | 0.12 | 3.48 | 3.63 |
| Butylenes | | | | 0.70 | 22.94 | 0.09 |
| 1,3-Butadiene | | | | 0.07 | | 0.07 |
| Total Gas | | | | 29.04 | 26.43 | 55.49 |
| Total Gas | | | | 29.04 | 26.43 | 55.49 |
| Total Liquid Products | | 63.83 | | | | |
| Coke | | | 7.14 | | | |
| Total | 100.00 | 63.83 | 7.14 | 29.04 | 26.43 | 55.49 |
| MB Checks | 100.00 | | 100.01 | | | |
| | | | | 55.47 | | 55.49 |

It has been shown that the fluidized catalytic cracking of a mercaptan oxidation by-product DSO in accordance with the present disclosure produces propylene.

Example 3

A disulfide oil and VGO blended sample was subjected to a fluidized catalytic cracking process using a Micro Activity Test (MAT) unit in accordance with the procedure of Example 1 as described above. Three runs were conducted at catalyst-to-oil (C/O) weight ratios of 5.4 and at a DSO/VGO volumetric ratio of 10/90, 30/70 and 50/50, and under conventional FCC conditions, i.e., 530° C. Table 4 indicates the product yields.

TABLE 4

| | Run 1 | Run 2 | Run 3 |
|---|---|---|---|
| DSO/VGO V % | 10/90 | 30/70 | 50/50 |
| Temperature ° C. | 530 | 530 | 530 |
| Catalyst/Oil Ratio | 5.4 | 5.4 | 5.4 |
| Gas Yields, W % | | | |
| H2 | 0.09 | 0.07 | 0.05 |
| Methane | 0.70 | 1.35 | 1.99 |
| Ethane | 1.03 | 1.76 | 2.49 |
| Ethylene | 4.51 | 7.29 | 10.06 |
| Propane | 6.15 | 4.80 | 3.46 |
| Propylene | 8.13 | 7.03 | 5.94 |
| Butanes | 4.44 | 3.47 | 2.51 |
| Butylenes | 7.23 | 5.78 | 4.33 |
| 1,3-Butadiene | 0.03 | 0.05 | 0.06 |
| Total Gas | 32.30 | 31.57 | 30.84 |
| Total Gas | 32.30 | 31.57 | 30.84 |
| Total liquid products | 66.50 | 65.90 | 65.30 |
| Coke | 1.17 | 2.51 | 3.85 |
| Total | 99.97 | 99.98 | 99.99 |

As indicated by the data in Table 4, at 530° C. and varying ratios of DSO to VGO, the fluidized catalytic cracking of the DSO/VGO blended sample yielded ethylene, propylene, and butylenes.

Example 4

An oxidized disulfide oil sample comprising water soluble ODSO components including alkyl-sulfoxidesulfonate (R—SO—SOO—OH), alkyl-sulfonesulfonate (R—SOO—SOO—OH), alkyl-sulfoxidesulfinate (R—SO—SO—OH) and alkyl-sulfonesulfinate (R—SOO—SO—OH) was subjected to a fluidized catalytic cracking process using a Micro Activity Test (MAT) unit, according to Example 1.

The test was conducted at a catalyst-to-oil (C/O) ratio of 2.92 and under conventional FCC conditions, i.e., 530° C. Table 5 indicates the product yields.

TABLE 5

| | Run 1 |
|---|---|
| Temperature ° C. | 530 |
| Catalyst/Oil Ratio | 2.92 |
| Gas Yields, wt. % | |
| H2 | 0.1 |
| Methane | 0.4 |
| Ethane | 0.3 |
| Ethylene | 14.7 |
| Propane | <0.1 |
| Propylene | 0.2 |
| Butanes | <0.1 |
| Butylenes | <0.1 |
| 1,3-Butadiene | 0.1 |
| Total Gas | 15.8 |
| Total Gas | 15.8 |
| Total liquid Products | 83.4 |
| Coke | 0.8 |
| Total | |

As indicated by the data in Table 5, at 530° C. and a catalyst-to-oil ratio of 2.92, the fluidized catalytic cracking of the ODSO samples, yielded 14.7 W % of ethylene, 0.2 W % of propylene and <0.1 W % butylenes.

It will be understood from the above description that the process of the present disclosure provides a cost effective and environmentally acceptable means for disposing of by-product disulfide oils, and can convert what may be essentially a low value refinery material into commercially important commodity products.

The process of the present invention has been described above and in the attached figures; process modifications and variations will be apparent to those of ordinary skill in the art from this description and the scope of protection is to be determined by the claims that follow.

The invention claimed is:

1. A process for the production of propylene from a hydrocarbon feedstream comprising disulfide oil compounds and oxidized disulfide oil compounds, the process comprising:
(a) introducing the hydrocarbon feedstream comprising the disulfide oil compounds and oxidized disulfide oil compounds into a fluidized catalytic cracking (FCC) unit for reaction to produce an FCC gaseous hydrocarbon products stream containing ethylene, and a cracked liquid hydrocarbon stream,
wherein the hydrocarbon feedstream comprises the disulfide oils and oxidized disulfide oils in a range of 1 V % to 100 V %,
wherein the hydrocarbon feedstream comprising the disulfide oil compounds and oxidized disulfide oil compounds is the reactant and the FCC gaseous hydrocarbon products stream containing ethylene and the cracked liquid hydrocarbon stream are products, and
wherein the disulfide oil compounds and oxidized disulfide oil compounds in the hydrocarbon feedstream are cracked to produce ethylene;

(b) introducing the FCC gaseous hydrocarbon products stream with a predetermined stoichiometric amount of butylenes into a metathesis unit;

(c) reacting the ethylene and the butylenes to produce propylene; and (d) recovering the propylene as a product stream from the metathesis unit, wherein the disulfide oil compounds are disulfide oils present in an effluent refinery hydrocarbon stream recovered downstream of a MEROX process, and wherein the oxidized disulfide oil compounds are catalytically oxidized disulfide oils present in an effluent refinery hydrocarbon stream recovered downstream of a MEROX process.

2. The process of claim 1 wherein the FCC gaseous hydrocarbon products stream is an ethylene-rich light olefins stream.

3. The process of claim 1 wherein a make-up ethylene stream is introduced into the metathesis unit.

4. The process of claim 1 wherein the hydrocarbon feedstream is mixed with one or more conventional FCC unit hydrocarbon feedstocks.

5. The process of claim 1 wherein the hydrocarbon feedstream is mixed with a vacuum gas oil stream.

6. A process for the production of propylene from a hydrocarbon feedstream comprising disulfide oil compounds and oxidized disulfide oil compounds, the process comprising:

(a) introducing the hydrocarbon feedstream comprising the disulfide oil compounds and oxidized disulfide oil compounds into a fluidized catalytic cracking unit for reaction to produce an FCC gaseous hydrocarbon products stream containing ethylene, and a cracked liquid hydrocarbon stream, wherein the hydrocarbon feedstream comprises the disulfide oils and oxidized disulfide oils in a range of 1 V % to 100 V %, wherein the hydrocarbon feedstream comprising the disulfide oil compounds and oxidized disulfide oil compounds is the reactant and the FCC gaseous hydrocarbon products stream containing ethylene and the cracked liquid hydrocarbon stream are products, and wherein the disulfide oil compounds and oxidized disulfide oil compounds in the hydrocarbon feedstream are cracked to produce ethylene;

(b) introducing the FCC gaseous products stream into a demethanizer unit to produce a C2+ stream and a combined hydrogen and methane stream;

(c) introducing the C2+ stream into a deethanizer unit to produce a C3+ stream and a combined ethane and ethylene stream;

(d) introducing the combined ethane and ethylene stream into a C2 splitter unit to produce an ethylene stream and an ethane stream;

(e) introducing the C3+ stream into a depropanizer unit to produce a C4+ stream and a combined propane and propylene stream;

(f) introducing the combined propane and propylene stream into a C3 splitter unit to produce a propylene stream and a propane stream;

(g) introducing the C4+ stream into a fractionation unit to produce an iso-butylene stream, a butylenes stream and a C5+ stream;

(h) introducing the ethylene stream from the C2 splitter unit and a predetermined stoichiometric amount of the butylenes stream into a metathesis unit;

(i) reacting the ethylene stream and the butylenes stream to produce a propylene product stream and a metathesis unit effluents stream;

(j) recycling the metathesis effluents stream to the FCC unit; and (k) recovering the propylene product stream from the metathesis unit, wherein the disulfide oil compounds are disulfide oils present in an effluent refinery hydrocarbon stream recovered downstream of a MEROX process, and wherein the oxidized disulfide oil compounds are catalytically oxidized disulfide oils present in an effluent refinery hydrocarbon stream recovered downstream of a MEROX process.

7. The process of claim 6, wherein the butylenes stream of step (g) comprises 1,3-butadiene, the process further comprising:

introducing the butylenes stream from step (h) and hydrogen into a selective hydrogenation unit to convert 1,3-butadiene into butylenes to produce a butylenes effluent stream comprising a portion of 1-butylenes; and introducing the butylenes effluent stream comprising a portion of 1-butylenes into a hydroisomerization unit to convert the 1-butylenes into 2-butylenes to produce an enhanced butylenes effluent stream that is the butylenes stream of step (i).

8. The process of claim 6, wherein a make-up butylenes stream is combined with the butylenes stream produced in the fractionation unit.

9. The process of claim 6, wherein the FCC gaseous hydrocarbon products stream is an ethylene-rich light olefins stream.

10. The process of claim 6, wherein a make-up ethylene stream is introduced into the metathesis unit.

11. The process of claim 6 further comprising recovering separate products including the cracked liquid hydrocarbon product stream, the combined hydrogen and methane stream, the ethane stream, the propylene stream, the propane stream, the C5+ stream, and the iso-butane stream.

12. The process of claim 6 wherein the hydrocarbon feedstream is mixed with one or more conventional FCC unit hydrocarbon feedstocks.

13. The process of claim 6 wherein the hydrocarbon feedstream is mixed with a vacuum gas oil stream.

* * * * *